(12) United States Patent
Sato et al.

(10) Patent No.: US 7,890,270 B2
(45) Date of Patent: Feb. 15, 2011

(54) OPTICAL SYSTEM FOR MEASURING METABOLISM IN A BODY, METHOD AND PROGRAM

(75) Inventors: Hiroki Sato, Fujimino (JP); Atsushi Maki, Fuchu (JP); Tsuyoshi Yamamoto, North Bethesda, MD (US); Masashi Kiguchi, Kawagoe (JP)

(73) Assignee: Hitachi Medical Corporation, Tokyo (JP)

( * ) Notice: Subject to any disclaimer, the term of this patent is extended or adjusted under 35 U.S.C. 154(b) by 164 days.

(21) Appl. No.: 12/392,207

(22) Filed: Feb. 25, 2009

(65) Prior Publication Data

US 2009/0163786 A1    Jun. 25, 2009

Related U.S. Application Data

(63) Continuation of application No. 11/570,558, filed on Dec. 13, 2006, now Pat. No. 7,516,021.

(51) Int. Cl.
 *G01N 31/00* (2006.01)
(52) U.S. Cl. ........................................ 702/32
(58) Field of Classification Search ................. 702/32; 600/328
 See application file for complete search history.

(56) References Cited

U.S. PATENT DOCUMENTS 6,907,279 B2 *  6/2005  Sato et al. .................... 600/322

FOREIGN PATENT DOCUMENTS

| JP | 2004-170958 | 6/2004 |
| WO | 02/32317 A1 | 4/2002 |

OTHER PUBLICATIONS

"Spatial and temporal analysis of human motor activity using noninvasive NIR topography" by Atsushi Maki, et al. Dec. 1995, vol. 22, No. 12.pp. 1997-2005.

"Noninvasive Cerebral Blood Volume Measurement During Seizures Using Multichannel Near Infrared Spectroscopic Topography" by Watanabe, et al. 1998. J. Epilepsy, vol. 11, No. 6., 335-340.

"Non-invasive assessment of Language Dominance with near-infrared spectroscopic mapping" by Eiji Watanabe, et al. Neuroscience Letters 256 (1998) 49-52.

"Multichannel Near-Infrared Spectroscopy in Depression and Schizophrenia: Cognitive Brain Activation Study" by Tomohiro Suto, et al. Biol PsycIIIatry 2004; 55:501-511.

* cited by examiner

*Primary Examiner*—Drew A Dunn
*Assistant Examiner*—Stephen J Cherry
(74) *Attorney, Agent, or Firm*—Mattingly & Malur, P.C.

(57) ABSTRACT

A living body light measuring device including plural light-radiating devices for radiating light to a head of a subject, plural light-receiving devices for detecting light which is transmitted through the head of the subject after radiation from the light-radiating devices, a calculator for calculating a change of concentration of oxidized and deoxidized hemoglobin in the head of the subject at a measurement point using a pair of each of the plural light-radiating devices and corresponding ones of the light-receiving devices. The calculator decides whether the oxidized hemoglobin concentration change and the deoxidized hemoglobin concentration change are statistically significant at each of the measurement points, and the display displays the decisions regarding the individual measurement points.

14 Claims, 12 Drawing Sheets

○ : INCIDENT POSITIONS

● : DETECTION POSITIONS

▤ : MEASUREMENT POSITIONS

LIVING BODY

OPTICAL SYSTEM FOR MEASURING METABOLISM IN A BODY, METHOD AND PROGRAM

This is a continuation application of U.S. Ser. No. 11/570,558, filed Dec. 13, 2006, now U.S. Pat. No. 7,516,021 the content of which is hereby incorporated by reference into this application.

TECHNICAL FIELD

The present invention relates to an optical organism measurement system that optically measures intracorporeal information, or especially, a change in the concentration of an optically absorbent material. More particularly, the present invention is concerned with an optical organism measurement system that uses data, which is obtained through optical organism measurement, to provide information that aids in assessing fitness.

BACKGROUND ART

The employment of light that is highly transmissive by an organism and exhibits a peak in light intensity in a wavelength band ranging from a visible region to a near-infrared region permits noninvasive measurement of intracorporeal information. This is attributable to the Lambert-Beer's law defining that a logarithmic value representing a measured light signal is proportional to the product of an optical length by a concentration. A technology of evolving the law and measuring a relative change in the concentration of intracorporeal oxidized hemoglobin (Hb), a relative change In the concentration of intracorporeal deoxidized hemoglobin (Hb), and a relative change in the concentration (hereinafter, a concentration change) of total hemoglobin (Hb) (sum total of the oxidized Hb and deoxidized Hb) has been developed.

A technology of simultaneously and non-invasively measuring a Hb concentration change at multiple points in the human cerebral cortex on the basis of the above technology has been proposed (Non-patent Document 1: "Spatial and temporal analysis of human motor activity using noninvasive NIR topography" by A. Maki et al. (1995)(Medical Physics 22, pp. 1997-2005).), and has prevailed in the fields of research and clinical practices. The document 1 has disclosed a method of measuring an Hb concentration change in the cerebral cortex so as to measure the cerebral functions of a human being. Specifically, along with the activation of the human sensor functions or kinetic functions, a blood volume in a cerebral region inside the cerebral cortex, which is responsible for the functions, locally increases. This causes the concentration of oxidized Hb or deoxidized Hb in the region to change, whereby the activities of the brain can be evaluated.

The technology is characteristic of being noninvasive and less-binding to a subject and permitting ready measurement of cerebral functions. Moreover, since the technology can evaluate the kinetics of blood circulation or the state of blood circulation, it is expected to be applied to an unprecedented medical field (clinical application). Examples of clinical applications that have reportedly proved useful include diagnosis of epilepsy (Non-patent Document 2: "Noninvasive cerebral blood volume measurement during seizures using multi-channel near-infrared spectroscopic topography" by E. Watanabe et al. (J. Epilepsy 11, pp. 335-340) and identification of a language-significant hemisphere (Non-patent Document 3: "Noninvasive assessment of language dominance with near-infrared spectroscopic mapping" by E. Watanabe et al. (1998) (Neurosci. Lett. 256, pp. 49-52).

In recent years, application to psychiatry has been encouraged. In patients suffering mental diseases such as depression and schizopherenia, Hb concentration changes observed through optical organism measurement reportedly exhibit a pattern different from the pattern exhibited by Hb concentration changes in sound people (Non-patent Document 4: "Multi-channel near-infrared spectroscopy in depression and schizopherenia: cognitive brain activation study" by T. Suto et al. (2004) (Biol. Psychiatry 55(5), pp. 501-511). In the document 4, oxidized Hb is used as an index, and waveforms specific to subjects suffering from respective diseases are presented. However, the reproducibility in an individual is uncertain. It is not easy to accurately assess the presence or absence of a disease in each subject or the symptom thereof. Moreover, whether individual differences in each Hb concentration change stem from differences in commitment to a task (psychological factor) or differences in the kinetics of blood circulation (physiological factor) has not been clarified.

DISCLOSURE OF INVENTION

Problem to be Solved by the Invention

In the past, the mainstream of diagnostic support to be achieved using cerebral activity signals has been comparison of mean values or variances obtained from multiple subjects with one another. However, in this case, it is hard to absorb individual differences. The precision in a diagnostic support technology is low. Improvement of the precision in the diagnostic support technology is a prospective issue that must be overcome and is assigned to the diagnostic support technology using the cerebral activity signals.

Means for Solving the Problem

Figure 3:
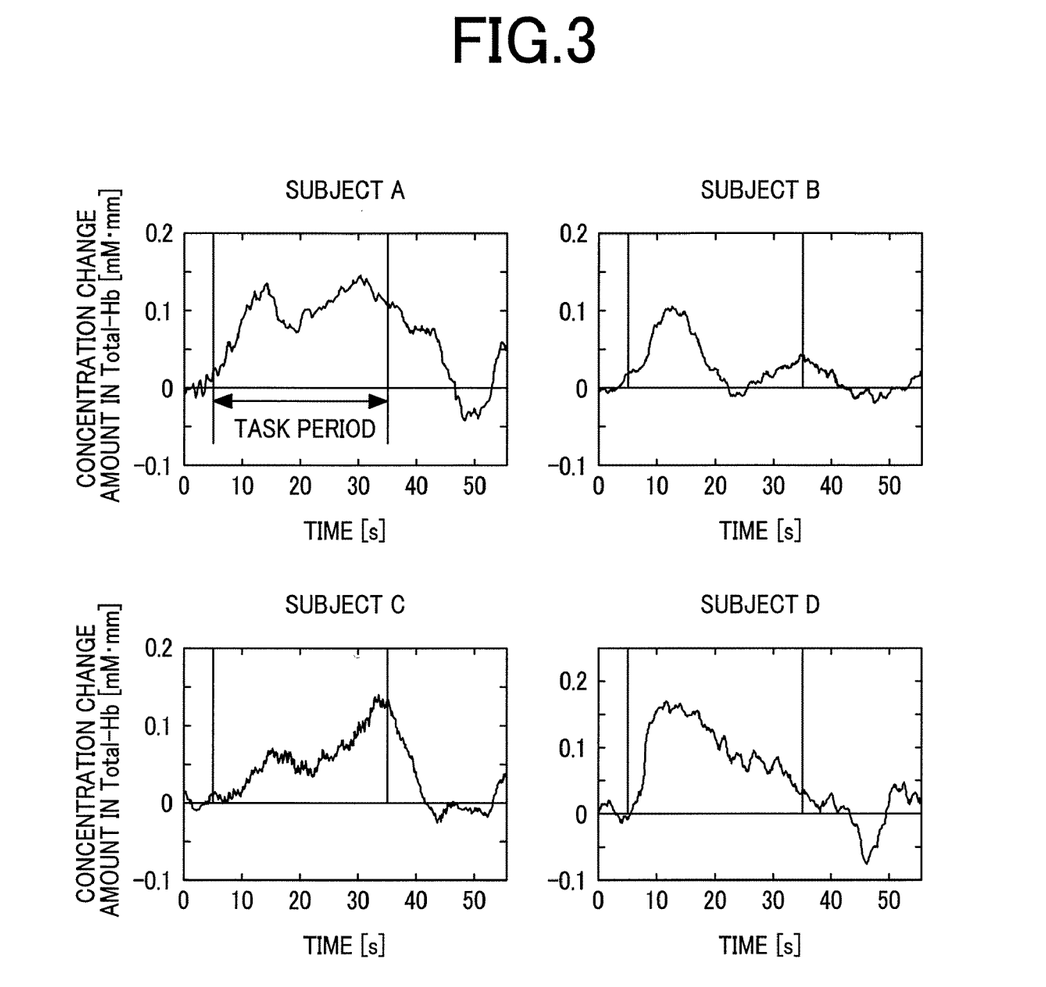
FIG. 3 shows an example of individual differences in a waveform representing a change in an oxidized Hb concentration change.

The present inventors measured thirty one sound people by assigning a task of finger motion. The activities of the motor area caused by the simple task of motion are regarded as an example of primitive activities, and are therefore hardly affected by a psychological factor that is a main factor causing individual differences. FIG. 3 shows the results obtained from four subjects (oxidized Hb concentration change). The tendency toward increase during a task period is observed in common, but the waveforms are largely different from subject to subject. Moreover, the waveforms representing a deoxidized Hb concentration change and a total Hb concentration change also vary among the subjects. Thus, even when the simple activities of the motor area that are thought to differ relatively slightly among individuals are taken for instance, the pattern of an Hb concentration change differs from subject to subject, though the subjects are sound people.

When the group of subjects is assessed as a whole, there is a possibility that a certain feature is observed. However, since diagnosis is performed on each person, it is different from statistical classification of results obtained from a population. In consideration of the individual differences in an Hb concentration change observed in the optically measured cerebral function data, individual diagnosis to be performed by matching with a prototype waveform (template) sampled from data of a population is not considered to be fully precise.

Figure 4:
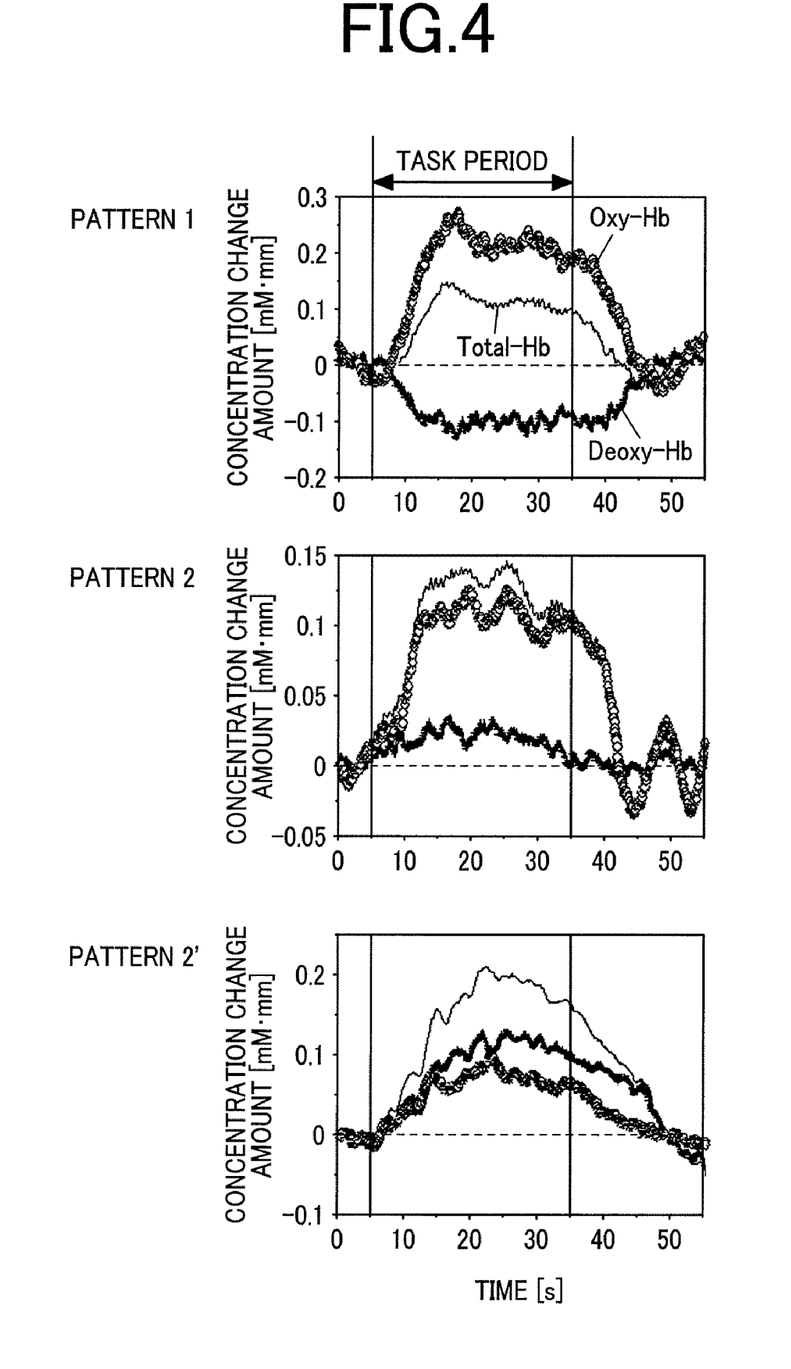
FIG. 4 shows an example of individual changes in a concentration change pattern representing an oxidized Hb concentration change, a deoxidized Hb concentration change, and a total Hb concentration change.

Generally, in many cases, an increase in the concentration of oxidized Hb, a decrease in the concentration of deoxidized Hb, and an increase in the concentration of total Hb are measured along with cerebral activities. The results of measurement performed by the present inventor et al. have, as shown in FIG. 4, revealed the diversity among Hb concentration changes and individual differences in the tendency of a change (increase or decrease). Table 1 lists the results of classification of the Hb concentration changes into patterns according to whether the change is an increase or a decrease. In the table 1, ↑ denotes an increase in the concentration of oxidized Hb, deoxidized Hb, or total Hb, and ↓ denotes a decrease therein. No significant change is denoted by -. The Hb concentration changes are classified into any of change patterns according to the combination of the increase, decrease, and no significant change.

TABLE 1

| | Breakdown of Hb concentration changes | | | |
| --- | --- | --- | --- | --- |
| Hb change pattern | Oxidized Hb concentration change | Deoxidized Hb concentration change | Total Hb concentration change | Percentage of subjects |
| 1 | ↑ | ↓ | ↑ | 56.4 |
| 2 | ↑ | ↓ | — | 9.7 |
| 3 | ↑ | ↑ | ↑ | 8.1 |
| 4 | ↑ | — | ↑ | 8.1 |
| 5 | ↑ | ↓ | ↓ | 4.8 |
| 6 | — | ↓ | — | 4.8 |
| 7 | ↑ | — | — | 3.2 |
| 8 | — | ↑ | — | 1.6 |
| Miscellaneous | | | | 3.3 |
| Total | | | | 100 |

Herein, the changes in three Hb concentrations (concentrations of oxidized Hb, deoxidized Hb, and total oxidized Hb) are classified according to three changes of an increase ↑, a decrease ↓, and no change -. Twenty seven patterns may be created. For convenience' sake, eight patterns of the highest appearing frequencies are numbered 1 to 8 and listed in the table. The rightmost column indicates a percentage out of thirty one subjects that exhibits each change pattern. Many change patterns match previous findings (an increase in the oxidized Hb concentration, a decrease in the deoxidized Hb concentration, and an increase in the total Hb concentration caused by the activities of the motor area). Since the Hb concentrations increase, decrease, or do not change independently of one another, a pattern exhibited by the combination of Hb concentration changes (hereinafter, Hb change patterns) varies depending on subjects.

Figure 5:
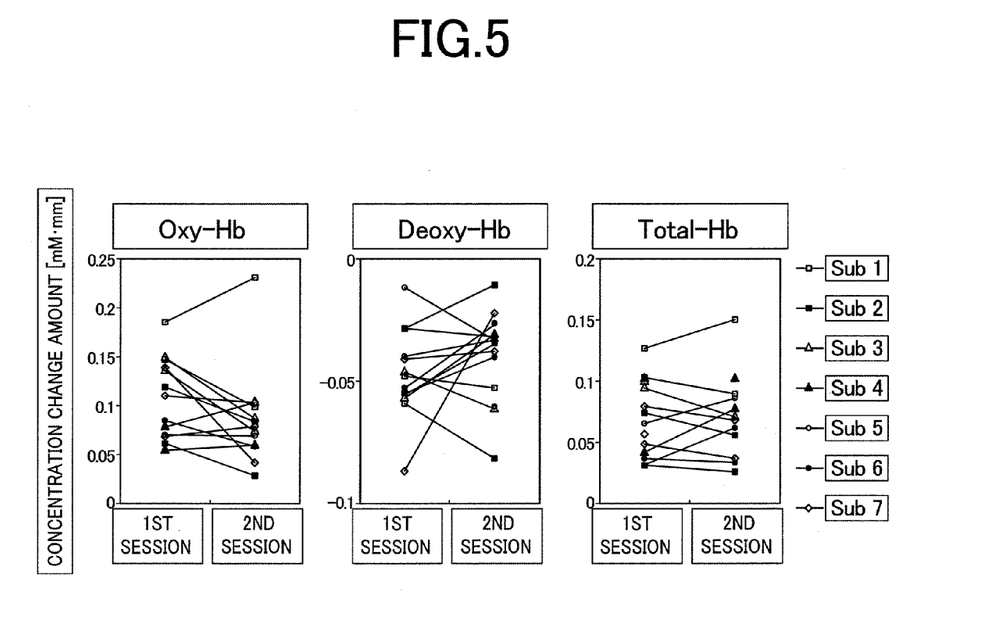
FIG. 5 shows the reproducibility of a change value (signal amplitude) in the concentration of oxidized Hb, deoxidized Hb, or total Hb.
Figure 6:
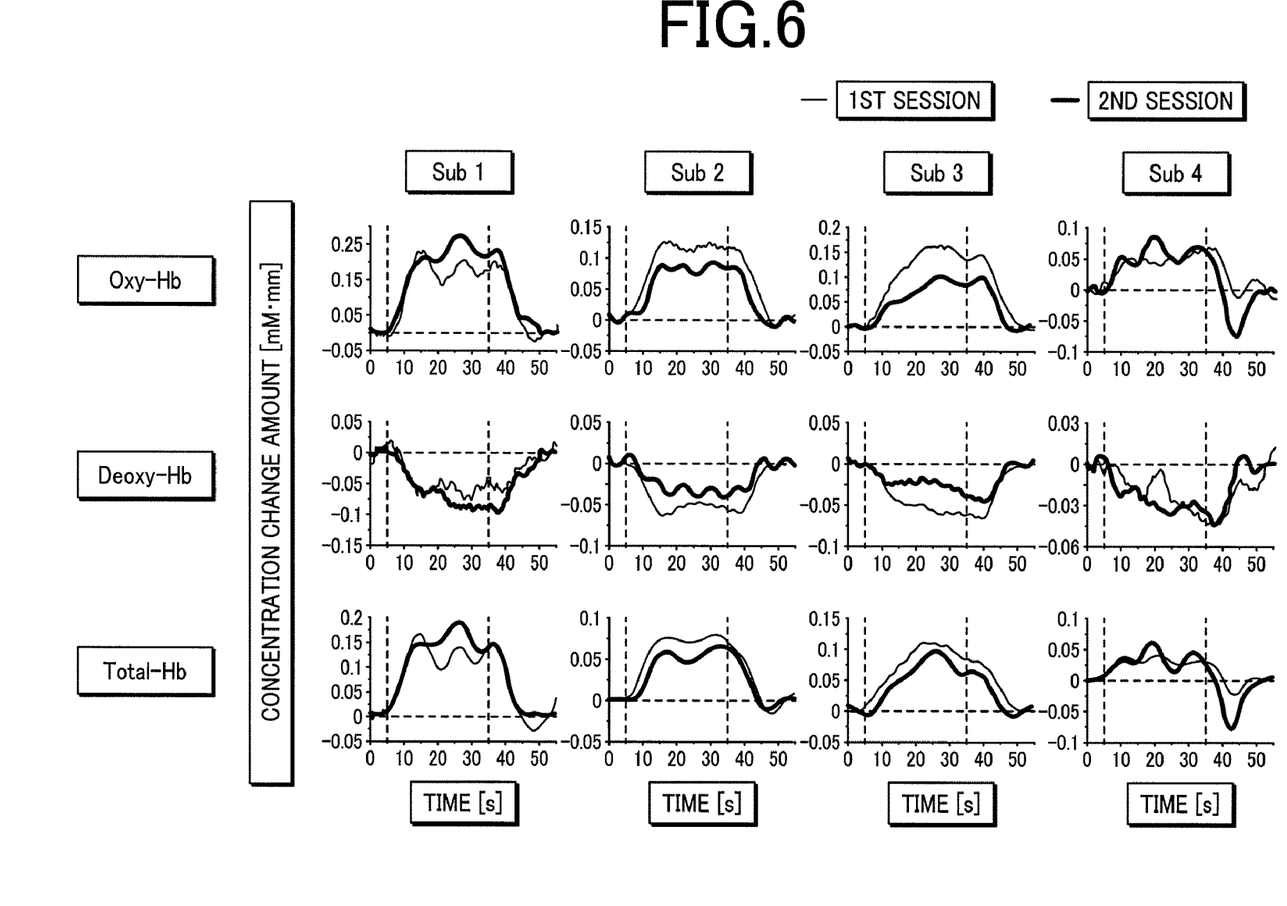
FIG. 6 shows a temporal change (activation time course) in the concentration of oxidized Hb, deoxidized Hb, or total Hb occurring in an active area.

In order to discuss the reproducibility of each Hb concentration change signal, the same measurement was repeatedly performed on seven subjects at intervals of approximately six months. As a result, the above Hb change patterns were nearly reproduced. Moreover, although the reproducibility of each Hb concentration change value (signal amplitude) is low (FIG. 5), the center region (active center) of a changing area (active area) is reproduced with an error of approximately 2 cm or less (Table 2). Since the spatial resolution offered by optical organism measurement ranges from 2 cm to 3 cm, the reproducibility of spatial information falls within a permissible range. Furthermore, when the temporal changes (activation time courses) in the respective Hb concentrations occurring in the active area are compared with others, they have high correlations (FIG. 6 and Table 3). This signifies that the activation time courses are helpful indices indicating a personal characteristic of a physiological condition.

TABLE 2

| | Oxidized Hb | Deoxidized Hb | Total Hb |
| --- | --- | --- | --- |
| Distance between active centers observed during two measurements (mean ± standard deviation) | 1.60 ± 1.21 | 1.86 ± 1.20 | 1.60 ± 0.91 |

TABLE 3

| | Oxidized Hb | Deoxidized Hb | Total Hb |
| --- | --- | --- | --- |
| Correlation coefficient between waveforms observed during two measurements (mean ± standard deviation) | 0.87 ± 0.14 | 0.83 ± 0.08 | 0.84 ± 0.13 |

The above results demonstrate that the method of measuring the same subject repeatedly using the same measurement method and discussing the individual time-sequential changes can provide more diagnostically helpful information than the method of comparing data acquired from each subject with a typical change pattern obtained from a population (for example, a change value or a waveform). In particular, for investigation of the reproducibility of akinetic change in blood circulation derived from the cerebral activities of an individual, (1) classification of Hb change patterns according on an increase or a decrease in each of the multiple Hb concentrations and (2) comparison of activation time courses (pieces of temporal information) in respective Hb concentration changes with others would prove effective.

Moreover, (3) comparison of active centers, where respective Hb concentration changes are observed, with others would prove effective. Incidentally, although three measured data items of the concentrations of oxidized hemoglobin, deoxidized hemoglobin, and total hemoglobin are employed, data items concerning increases or decreases in the concentrations of the oxidized hemoglobin and deoxidized hemoglobin may be used to provide diagnostically helpful information.

The optical organism measurement system in accordance with the present invention places emphasis on a time-sequential change in an individual obtained from data acquired by the optical organism measurement system. Moreover, the optical organism measurement system produces and displays helpful information representing a change in the condition of each person, and effectively supports diagnosis of the person. The optical organism measurement system includes a means for calculating and recording Hb concentration changes using measured light signals, and a means for simultaneously reading and displaying multiple record data items measured at different time instances. Moreover, the optical organism measurement system includes: a means for classifying a combination of two or more Hb concentration changes (for example, an oxidized Hb concentration change and a deoxidized Hb concentration change) into any of change patterns (for example, pattern 1 representing an increase in an oxidized Hb concentration, a decrease in a deoxidized Hb concentration, and an increase in a total Hb concentration) on the basis of each data (representing respective Hb concentration changes), and displaying the change pattern in the form of symbols, an image, or a graph; and a means for displaying two or more data items, which are measured at different time instants, in the form of an image, a graph, or numerical values concurrently with an index calculated from one Hb concentration change or two or more Hb concentration changes (for example, total Hb=oxidized Hb+deoxidized Hb). Thus, the optical organism measurement system provides an examining person with compressed or simplified information.

Effect of the Invention

According to the present invention, multiple different pieces of information are integrated in order to provide new information. This lightens manipulations an examining person has to perform and permits ready or accurate diagnosis.

Multiple data sets acquired at different time instants by measuring the same subject are integrated, and the resultant information is presented to an examining person in an easy-to-understand manner. Ready diagnosis of a change in the condition of each subject can be aided.

Moreover, since the present invention makes it possible to effectively grasp a time-sequential change in an individual, it can be applied to evaluation of the results of rehabilitation or image training or diagnosis.

BRIEF DESCRIPTION OF THE DRAWINGS

FIG. 10 show examples of display screen images concerning comparison of waveforms, FIG. 10A is plotted by overlapping multiple contrast data items, and FIG. 10B displays a mean-value waveform and a standard deviation which are calculated using multiple data items;

BEST MODE FOR CARRYING OUT THE INVENTION

Figure 1:
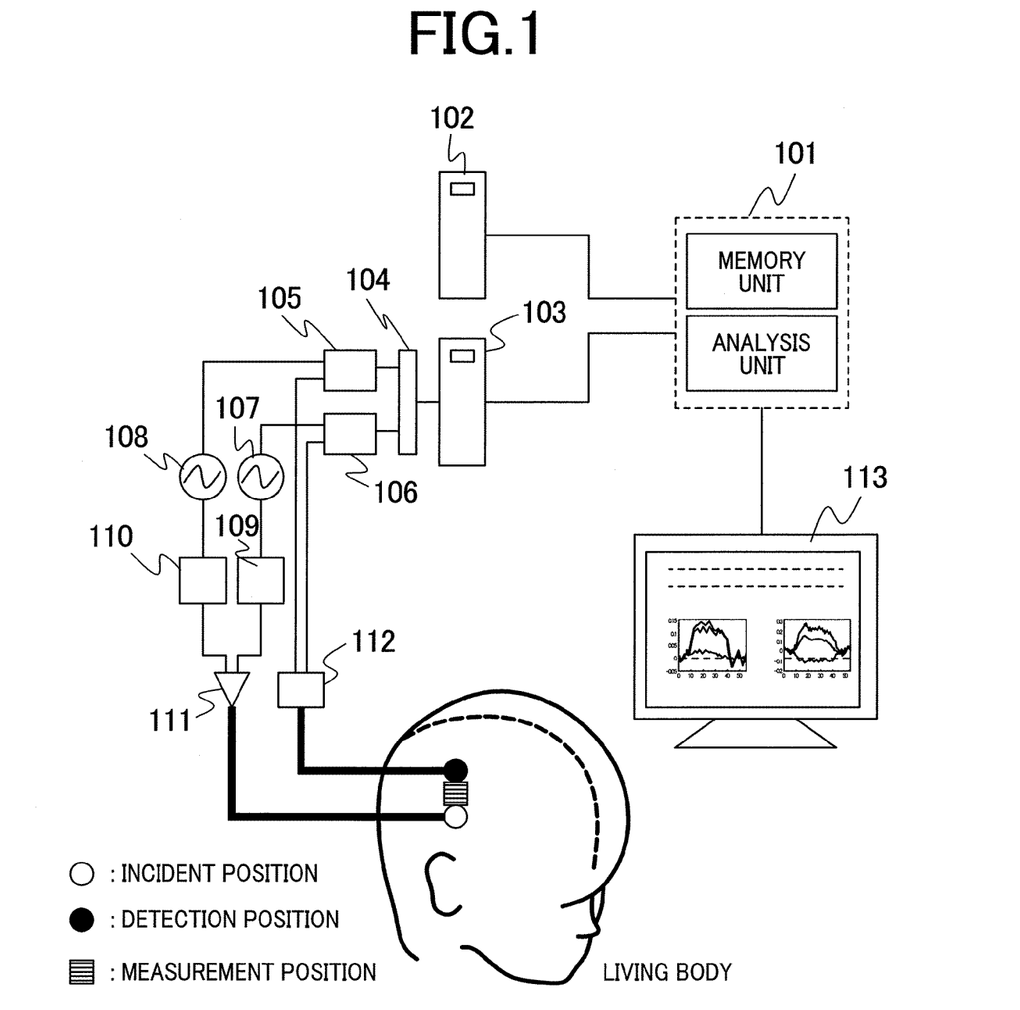
FIG. 1 is a block diagram showing an embodiment of an optical organism measurement system in accordance with the present invention.

Referring to the drawings, an embodiment of the present invention will be described below. FIG. 1 is a block diagram showing the outline of an optical organism measurement system in accordance with the present invention. The optical organism measurement system includes: a control unit 103 realized with an electronic computer represented by a personal computer or a workstation; two laser diodes 109 and 110 offering mutually different wavelengths; oscillators 107 and 108 that produce signals with which light waves produced by the two laser diodes are modulated at different frequencies; an optical mixer 110 that mixes two light waves having different peak wavelengths; a light irradiation means for irradiating light, which is produced by the optical mixer 110, to a light incident position on a living body over an optical fiber; a photodetector 111 that detects mixed light at a light-detected position (approximately 3 cm away in this embodiment) appropriately separated from the light irradiation means; lock-in amplifiers 105 and 106 into which a modulation frequency for the oscillator is transferred as a reference signal; and an analog-to-digital converter 104 that converts transmitted light signals, which represent light waves being transmitted from the lock-in amplifiers and falling with different wavelength bands, from an analog form to a digital form.

Figure 2:
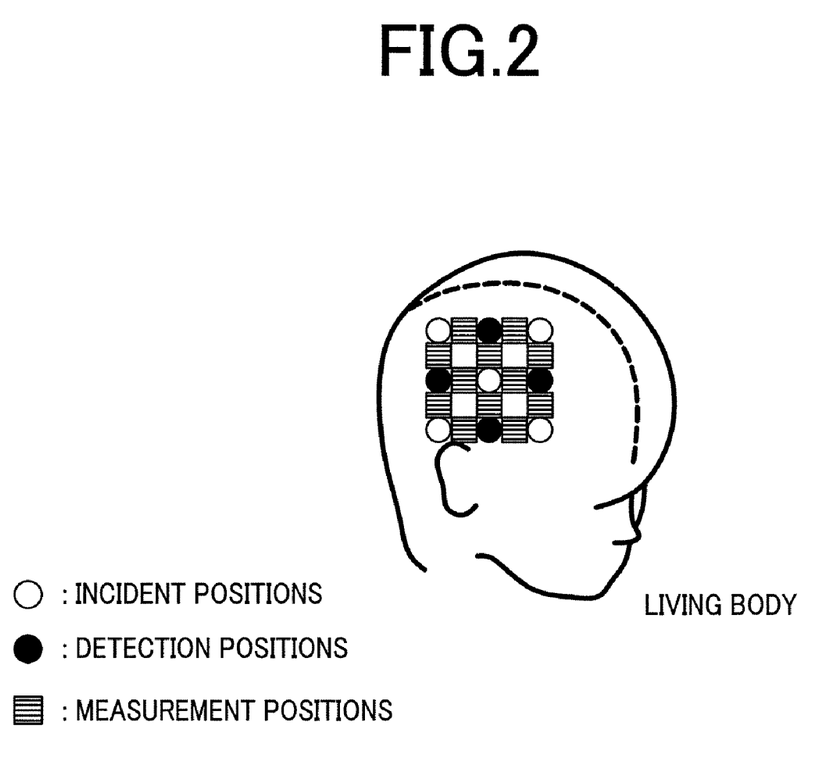
FIG. 2 illustratively shows an example of the embodiment (simultaneous measurements at multiple points) of the optical organism measurement system in accordance with the present invention.

The largest number of pieces of information on metabolites is obtained at a substantially intermediate position between the light source and detector. For convenience' sake, the substantially intermediate position shall be regarded as a measurement point. However, the measurement point (measurement area) is determined based on a sensitivity distribution measured by the pair of the light source and detector. In FIG. 1, only one measurement position is shown. Since the oscillator is used to separate multiple light signals from one another, an optical organism measurement system having multiple light incident positions and light-detected positions arrayed as shown in FIG. 2 can be used to measure multiple positions in practice.

In the present embodiment, the oscillator is used to separate multiple light signals from one another. Alternatively, the oscillator may not be used but pulsed light may be used to separate light signals from one another according to the lighting timings. The transmitted light signals representing light waves that fall within different wavelength bands are analog-to-digital converted by the analog-to-digital converter 104, and then transferred to and stored in the control unit 103. The control unit 103 calculates Hb concentration changes at each region to be measured on the basis of the transmitted light signals. The Hb concentration changes are transferred to and stored in a data accumulation server 102 together with the original signals (transmitted light signals). Preferably, the measured data should also be stored in a storage medium such as an IC card other than the data accumulation server, and each person should carry the storage medium.

Both data measured by the control unit 103 and previous measured data of the same subject stored in the data accumulation server 102 or the storage medium such as an IC card are read and stored in a memory unit included in a diagnostic aid 101. An analysis unit included in the diagnostic aid 101 calculates spatial information (activation map) on each activity (each Hb concentration change) and temporal information (activation time course) thereon using the multiple data items, and displays the pieces of information on a display 112 in the form of symbols, numerical values, an image, or a graph.

Figure 7:
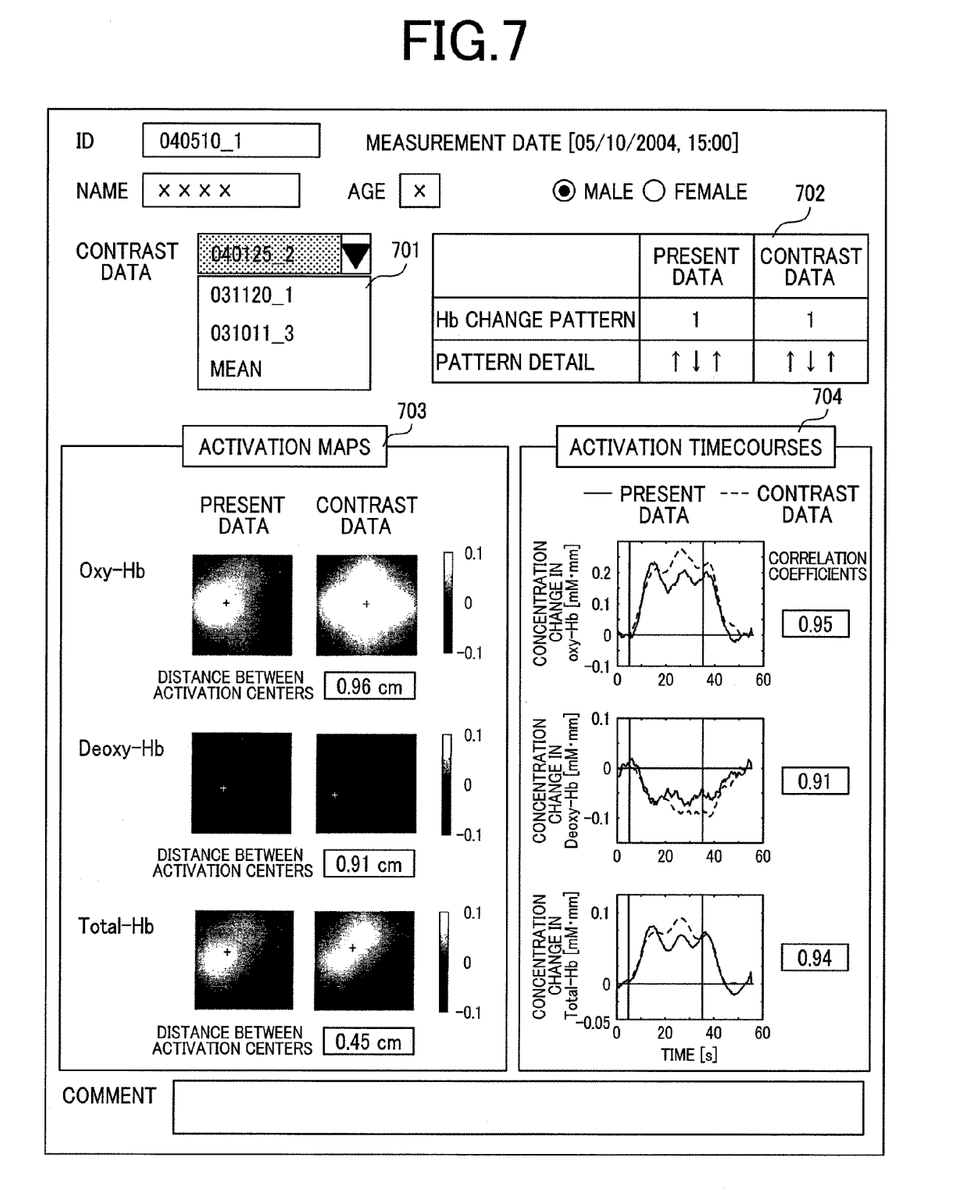
FIG. 7 shows an example of a display screen image on the optical organism measurement system in accordance with the present invention.
Figure 8:
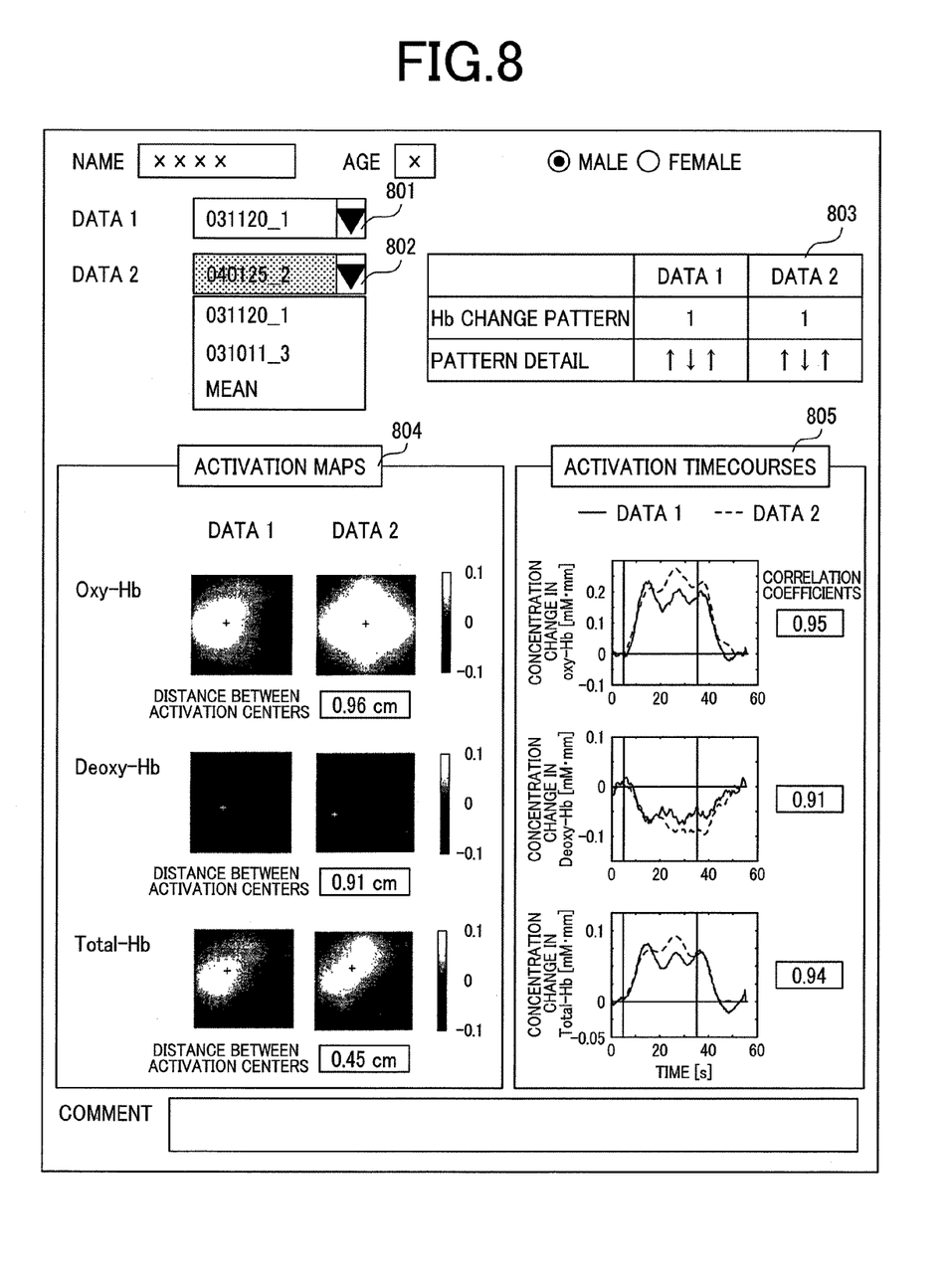
FIG. 8 shows an example of a display screen image on the optical organism measurement system in accordance with the present invention.
Figure 9:
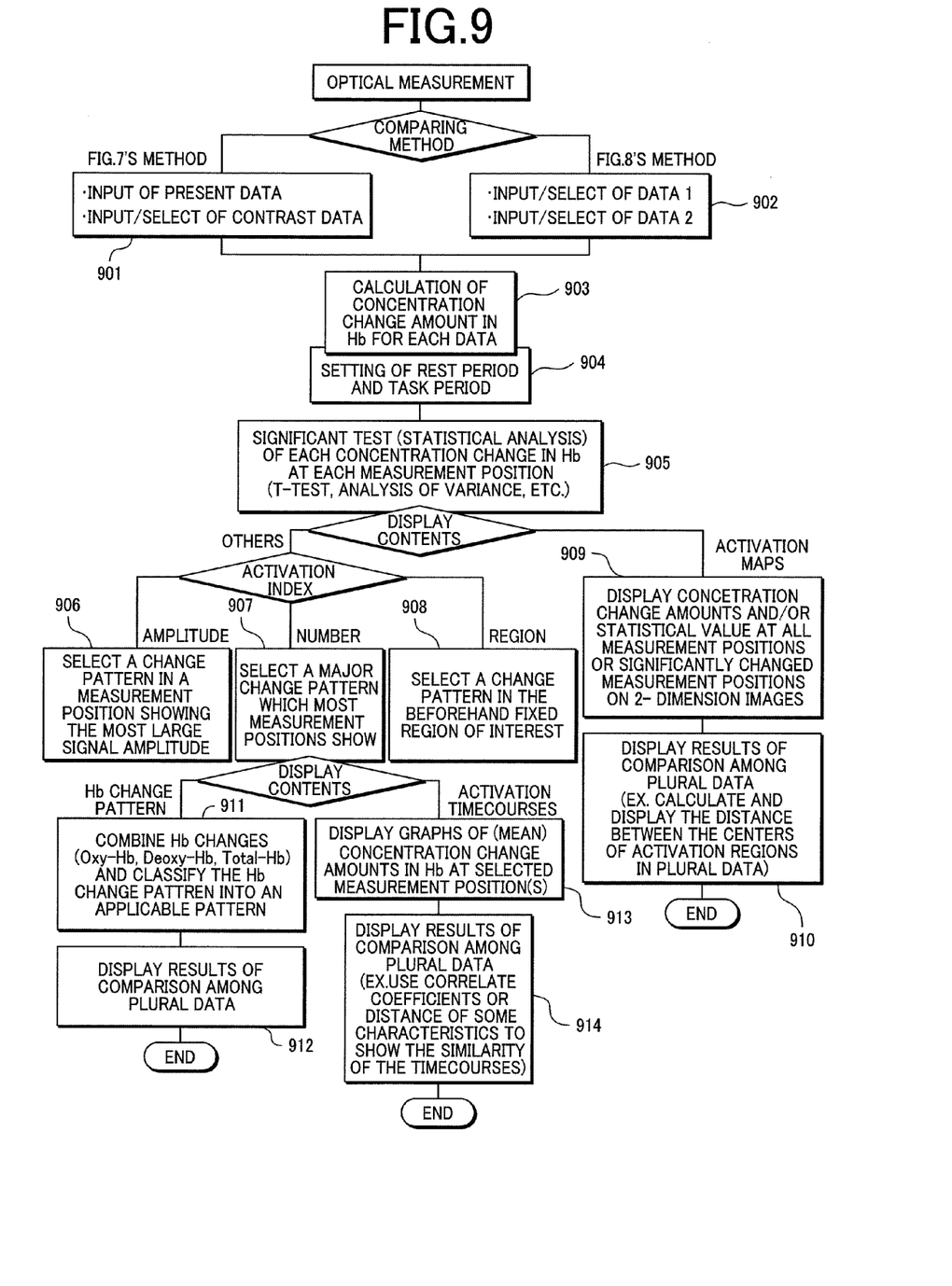
FIG. 9 is a flowchart describing major processing to be performed by a diagnostic aid.

FIG. 7 and FIG. 8 show examples of the contents of display achieved in a case where Hb concentration changes derived from cerebral activities are simultaneously measured at multiple points. FIG. 9 is a flowchart describing data processing that ends with display. The data processing described in the flowchart may be executed by installing a program that allows a conventional optical organism measurement system to execute the processing.

In an initial process, first, a data comparison form is selected. FIG. 7 shows a display screen image displayed so that data measured immediately previously can be compared with any previous data (FIG. 7 form). FIG. 8 shows a display screen image displayed so that any previous data items selected can be compared with each other (FIG. 8 form). Herein, the number of data sets to be compared with each other is two. Alternatively, two or more data sets may be compared with one another. At step 901 of selecting and transferring data, an interface like a pull-down menu 701 shown in FIG. 7 is used to select and read data to be compared with currently measured data from among a group of previous data items stored in the data accumulation server or a storage medium such as an IC card.

Likewise, at step 902, pull-down menus 801 and 802 shown in FIG. 8 are used to select and read two data sets from the data accumulation server or the storage medium such as an IC card. When Mean is selected from the pull-down menu, means of multiple data items acquired from the same subject are worked out, and can be compared with a general tendency (all of previous data items) observed in the subject. The means are therefore useful. Multiple data items may be selected from among all of previous data items, and then averaged. The format of data to be selected and transferred to the diagnostic aid 101 may be determined arbitrarily. In the case of original signals that are transmitted light signals or transmitted light intensity data items, Hb concentration changes are calculated at step 903.

Thereafter, at step 904, a rest period and an active period are designated. A designation method may be not only arbitrary designation by a user but also automatic designation of an optimal active period using a signal waveform. For example, a range that may be designated as an active period and a length of the active period may be designated, and a period during which a mean Hb concentration change value (absolute value) is maximized may be calculated and designated. The parameters of the rest period and active period are used to decide at step 905 whether an oxidized Hb concentration change, a deoxidized Hb concentration change, and a total Hb concentration change measured during the active period are significant.

For example, assuming that a task is assigned repeatedly multiple times, a mean Hb concentration change value (baseline) relevant to the rest period succeeding each task time and a mean Hb concentration change value (signal amplitude) relevant to the task (active) period are calculated. Differences between the mean values relevant to multiple baseline periods and the mean values relevant to multiple active periods are evaluated relative to each measurement point according to a statistical technique such as t-test or analysis of variance. Moreover, a correlation coefficient relative to a temporal change in an Hb concentration expected during an active period or a non-parametric statistical technique may be used to evaluate the presence of a significant Hb concentration change (activity). The present embodiment need not be limited to any specific statistical technique. Moreover, some statistical techniques do not require designation of the rest period and active period. After testing on an activity (significance) is completed, the processing proceeds according to the contents of display.

In the example of display according to the present embodiment, Hb change patterns based on data sets to be compared with each other (702 in FIG. 7 or 803 in FIG. 8), activation time courses (704 in FIG. 7 or 805 in FIG. 8), and activation maps (703 in FIG. 7 or 804 in FIG. 8) are displayed. Data sets measured during respective periods may be displayed synchronously with each other or mean values may be displayed. The display will be detailed below.

If the contents of display include Hb change patterns or activation time courses, a typical tendency of change (an increase or decrease in each Hb concentration) must be determined during each measurement. This is because the present embodiment is intended to simultaneously measure many points and all the measurement points rarely show the same tendency of change. Several methods are available as a method for determining how to select a typical activity (a tendency of change employed in evaluation). For example, a change occurring at a measurement point at which the largest signal amplitude (statistical value, a mean change value, a maximum change value, etc.) is measured from each Hb may be adopted as it is at step 906.

Otherwise, a change (an increase or decrease) observed at the largest number of measurement points among all measurement points may be adopted as it is at step 907. If no significant change is observed at any of the measurement points, a category of No Change may be adopted. Moreover, if a region to be examined is fixed in advance, a measurement point corresponding to the region may be selected and a change observed at the measurement point may be adopted (step 908).

Thereafter, if Hb change patterns are displayed, a combination of Hb concentration changes is classified into any of Hb change patterns at step 911. For example, a mean value of each Hb concentration change occurring during a task period is significantly smaller than that during a rest period, the change is displayed as a decrease (↓). If the mean value is significantly larger, the change is displayed as an increase (↑). If the mean values of the Hb concentration change occurring during the task and rest periods respectively have no significant difference between them, no change (-) is displayed. Thus, a combination of increases or decreases that are Hb concentration changes is displayed using the symbols (702 in FIG. 7 or 803 in FIG. 8). Hb change patterns into which current data and contrast data or data 1 and data 2 are classified are displayed side by side, whereby whether a time-sequential change in a fundamental Hb change pattern occurs in a subject can be decided.

As a diagnostic case, a case where a subject who have exhibited an increase in the concentration of oxidized Hb and a decrease in the concentration of deoxidized Hb shows an increase in both the concentrations of the oxidized Hb and deoxidized Hb will be discussed below. In this case, a blood flow velocity was higher than a speed of oxygen consumption in blood and the concentration of deoxidized Hb decreased. However, the currently obtained results demonstrate that a rise in the blood flow velocity is small but deoxidization derived from the oxygen consumption is facilitated. From the viewpoint that the blood flow velocity gets slower, a condition that the flow of blood is stagnated or the resilience of a blood vessel is degraded is conceivable. This can be used as findings to diagnose the subject.

Moreover, when an activation time course is displayed, the changes selected at step 906, 907, or 908 are displayed. The display screen image employed in the present embodiment (704 in FIG. 7 or 805 in FIG. 8) shows the results of current measurement or the data 1 using a bold line, and shows previously measured contrast data or the data 2 using a thin line. The axis of ordinates reads Hb concentration change values (mM/mm), and the axis of abscissas reads times (sec). For display, an activation time course observed at one selected measurement point may be employed or an activation time course sampled from a mean of data items obtained at multiple measurement points may be employed (step 913).

Figure 10A:
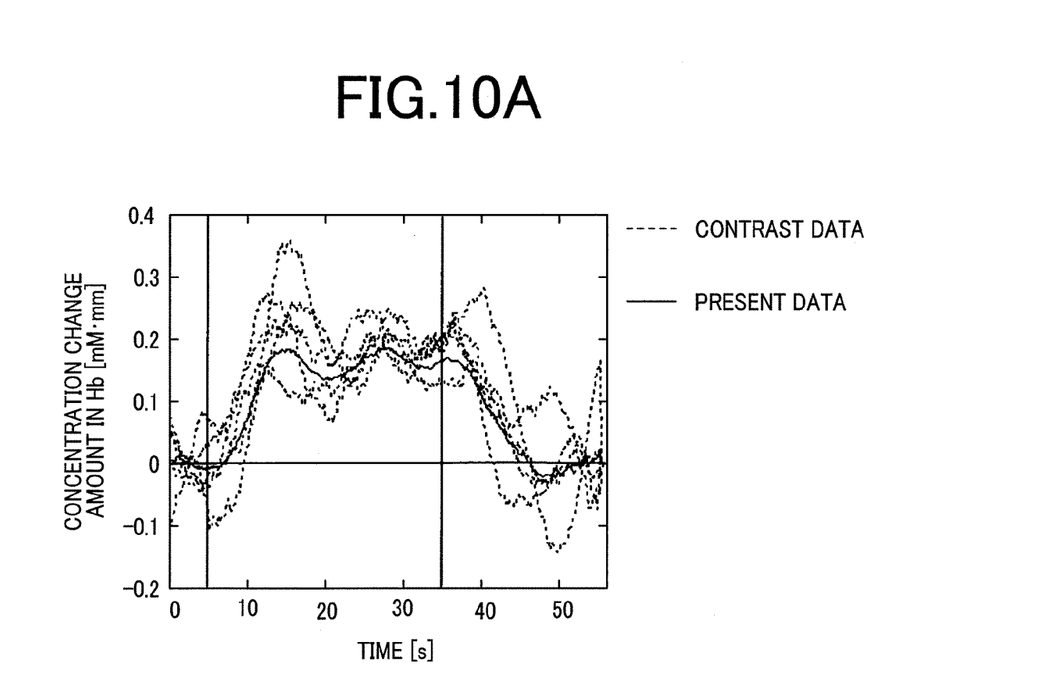
Figure 10B:
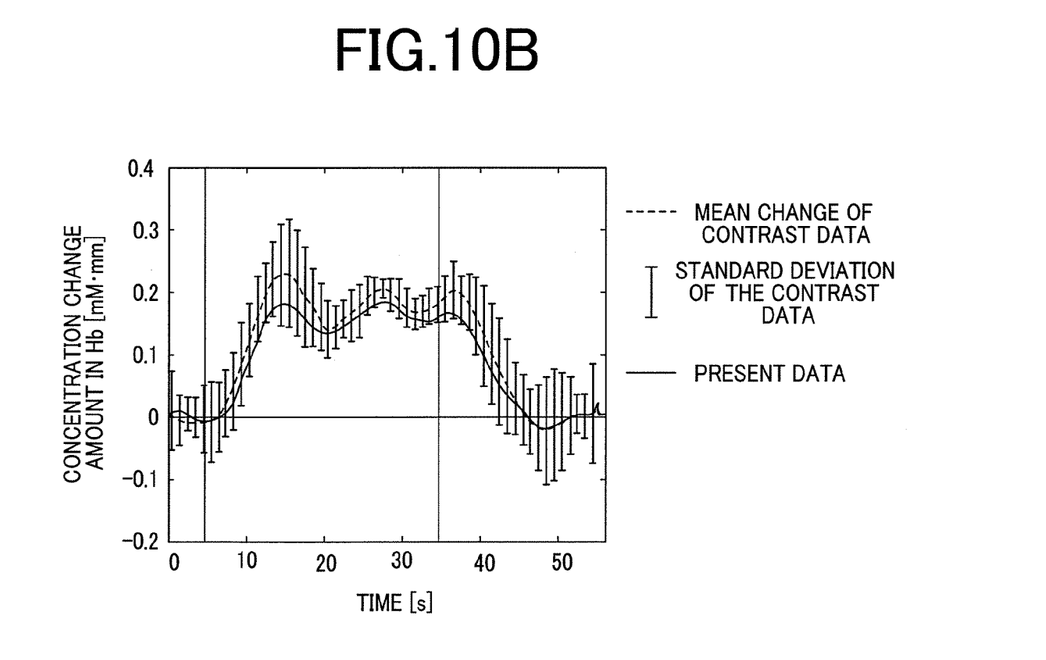
Figure 11A:
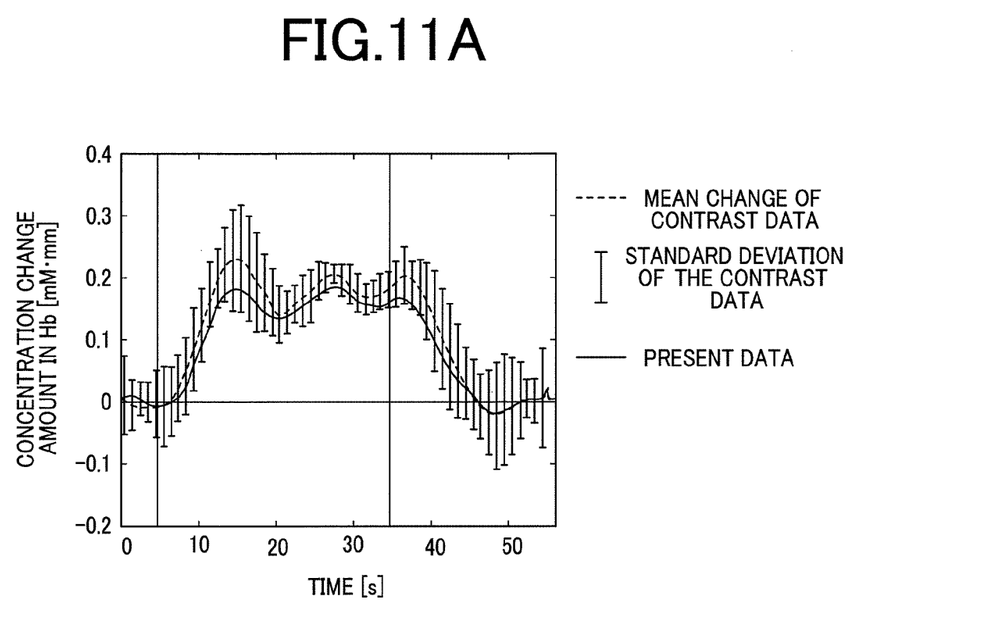
FIGS. 11A and 11B show examples in which a pattern of an oxidized Hb concentration change in the same subject changes drastically (from FIG. 11A to FIG. 11B)

For simplification of comparison of multiple data items with each other, for example, multiple previous data items and current data may be, as shown in FIG. 11A, displayed to overlap. This display method makes it possible to readily decide whether the current data agrees with any of the previous results. Moreover, when a mean-value waveform and standard deviations are calculated from multiple data items (FIG. 10B), current data to be discussed is plotted to overlap the mean-value waveform and standard deviations. In this case, to what extend the current data deviates from the previous tendency or diagnostically helpful information is provided. At step 914, the results of comparison of activation time courses with each other are displayed concretely using numerical values.

In the examples of display according to the present embodiment, a correlation coefficient is displayed on the right side of a graph in order to present the similarity between waveforms. Aside from the correlation coefficient, a feature value representing a feature of a waveform (latent time, rise time, angle, amplification, etc.) may be indicated numerically. Moreover, a mean-value waveform (and a variance) representing previously obtained data items and a waveform representing current data may be statistically compared with each other, and the reproducibility of the waveform may be displayed numerically. This would prove helpful. As for evaluation of the reproducibility of an activation time course, a range of values to be attained in a sound condition may be designated automatically or manually. An alarm may be given in any form in case a value deviates from the range. A facility for giving such an alarm would be found helpful.

Figure 11B:
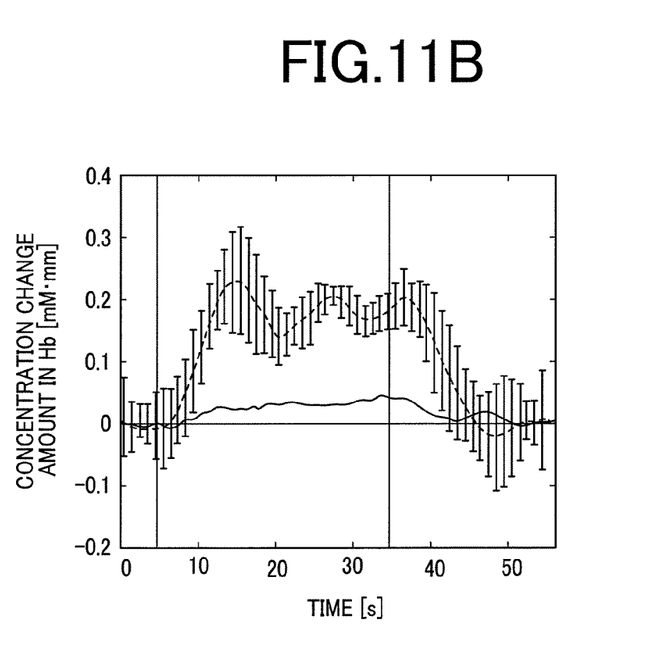

Comparison of waveforms with one another in terms of similarity corresponds to finer comparison of Hb activity patterns with each other. Even when similar Hb activity patterns are displayed, a change in the kinetics of blood circulation can be found out based on a fine difference between the patterns. As shown in FIG. 11, in an unusual case, a state in which an activation time course of the concentration of oxidized Hb is plotted in a mean-value range (FIG. 11A) may be changed to a state in which the activation time course is plotted away from the mean-value range (FIG. 11B). In this case, since an increase in a blood volume derived from cerebral activities is decelerated, the plasticity of a blood vessel may be degraded or a physiological change caused by the cerebral activities may be transformed (for example, from a change that is mainly occupied by an increase in a blood volume to a change that is mainly occupied by oxygen consumption).

Figure 12:
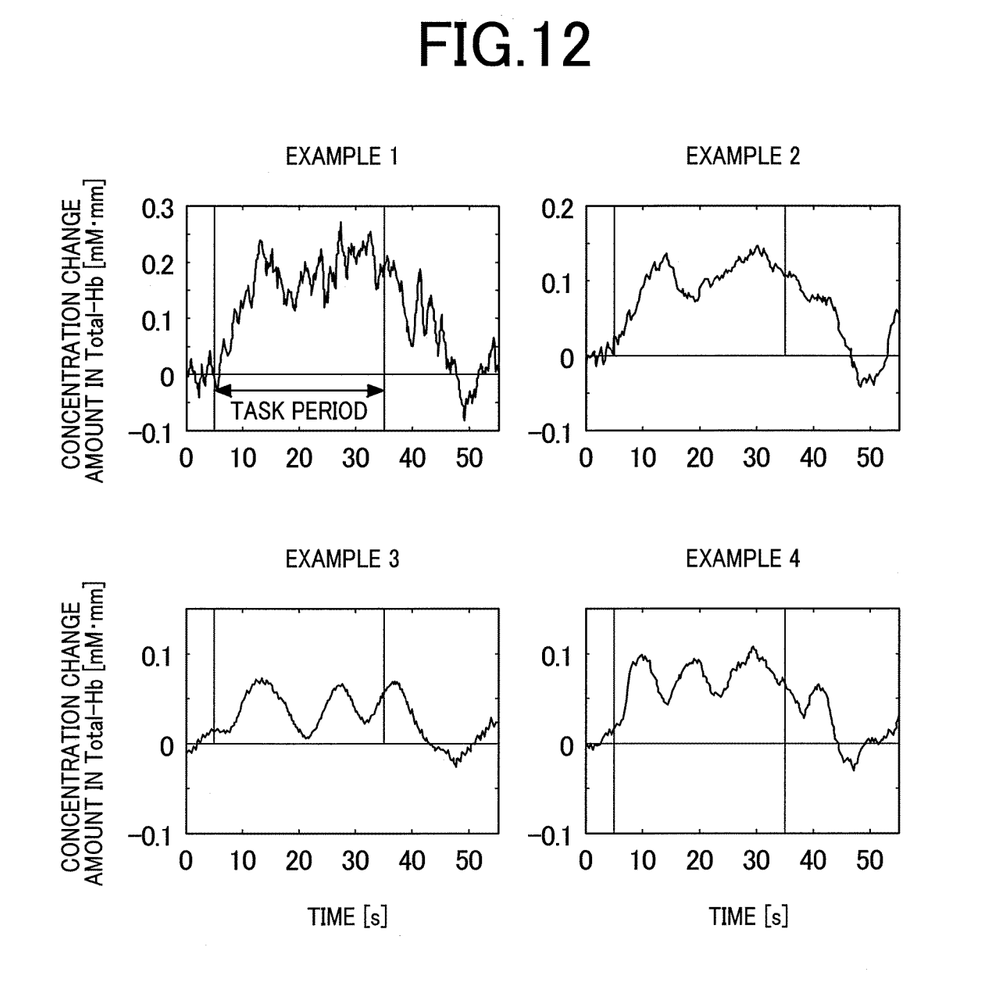
FIG. 12 shows individual differences in a waveform representing an Hb concentration change and being affected by system-related noises and other physiological noises.

Furthermore, the similarity between activation time courses observed in the same subject may be used to improve a signal processing method. As shown in FIG. 12, a waveform representing an Hb concentration change in a subject differs from person to person. However, the individual differences include not only individual differences in a pattern of cerebral activities but also system-related noises and other physiological noises. Therefore, an appropriate processing method should preferably be used to sample a change stemming from cerebral activities. Specifically, when Hb concentration changes are calculated based on measured original signals (transmitted-light intensities), several parameters can be optimized using the similarity between activation time courses. For example, when a fitting curve is calculated as a baseline, which is needed to calculate an Hb concentration change, on the basis of values detected for several seconds preceding application of stimulation and values detected for several seconds succeeding the application, a period preceding the application of stimulation, a period succeeding the application thereof, and a degree of an equation representing the fitting curve are determined in order to maximize the correlation coefficient between the Hb concentration changes occurring during the stimulation periods. Moreover, after each Hb concentration change is calculated with any value defined as a baseline, if the Hb concentration change is corrected through frequency filtering, a filter is defined using the correlation coefficient between the Hb concentration changes occurring during the respective stimulation periods, as a reference.

Next, the activation map will be described below. In the activation map displayed according to the present embodiment (703 in FIG. 7 or 804 in FIG. 8), the results of measurement performed on the same subject on different dates are displayed side by side (the concentrations of oxidized Rb, deoxidized Hb, and total Rb from above). The strength of an activity is expressed with a signal amplitude at each measurement point (a mean Hb concentration change value obtained during a task period), and indicated using a right-hand color bar as a scale (step 909). Alternatively, a maximum Hb concentration change value obtained during an active period may be indicated. As Hb concentration changes are classified into any of Hb change patterns, so significant Hb concentration changes derived from a task may be statistically evaluated and the resultant statistical values may be indicated, or a measurement point at which a statistically significant change is observed may be selected and a signal amplitude detected thereat may be indicated. At step 910, the results of comparison of activation maps with each other are displayed concretely.

For example, when a center region of an activity (active center or activated center) is indicated in an activation map, a change in the activated center occurring along with the passage of time is seen. A method of determining the activated center includes a method of selecting a measurement point at which the most intensive activity is observed and a method of calculating a barycenter of an active area, where a significant change is observed, using a signal amplitude or a statistical value as a reference. On the display screen employed in the present embodiment, the barycenter (activated center) calculated using the signal amplitude as a reference is indicated with +, and the distance (cm) between activated centers sampled from respective data items is indicated below a map. Similarly to the activation time course, if the reproducibility of the position of an activated center is deviated from a reproducible range that is measured in a sound condition and that is automatically or manually designated, an alarm may be given. A facility for giving such an alarm would be found useful. In the case of a sound person, the activated center is reproduced nearly at the same position (Table 2). This may be helpful in checking whether a correct region is measured or in correcting a position.

In case of a subject who suffers from cerebral infarct or has some function thereof disordered, the disordered function may be compensated by other cerebral region through rehabilitation. The compensating region may be observed. During image training or any other functional training, the spread of an active region is observed along with the progress of the training, and the effect of the training can be fed back.

INDUSTRIAL APPLICABILITY

Since the present invention makes it possible to readily and effectively grasp a time-sequential change occurring in each person, it can therefore be applied to evaluation of an effect of rehabilitation or training or diagnosis.

The invention claimed is:

1. A living body light measuring device, comprising:
plural light-radiating means from which light is radiated to a head of a subject,
plural light-receiving means for detecting light which is transmitted through the head of the subject after radiation from the light-radiating means,
a calculator for calculating a change of concentration of oxidized hemoglobin and a change of concentration of deoxidized hemoglobin in the head of the subject at a measurement point comprising a pair of each of the plural light-radiating means and corresponding ones of the light-receiving means, wherein the measurement point includes a signal detected by the light-receiving means,
a display for displaying the calculations obtained from the calculator,
wherein the calculator decides whether the oxidized hemoglobin concentration change and the deoxidized hemoglobin concentration change are statistically significant at each of the measurement points, and
the display displays the decisions regarding the individual measurement points.

2. The living body light measuring device according to claim 1, wherein the display displays the decision varied in accordance with at least one of the significance of matter that the oxidized hemoglobin concentration change, the significance of matter that the deoxidized hemoglobin concentration change, and the significance of the matter that each of the oxidized hemoglobin concentration change and the deoxidized hemoglobin concentration change.

3. The living body light measuring device according to claim 1, wherein the calculator decides whether the oxidized hemoglobin concentration change and the deoxidized hemoglobin concentration change are each significant on the basis of statistical analysis.

4. The living body light measuring device according to claim 1, wherein, in the statistical analysis, any one of a parametric test and a nonparametric test is used.

5. The living body light measuring device according to claim 1, which further comprises a setting-up section for setting up the decision made by the calculator.

6. The living body light measuring device according to claim 1, which further comprises a setting-up section in which an activity period is inputted for each of oxidized hemoglobin and deoxidized hemoglobin,
wherein the calculator decides whether the oxidized hemoglobin concentration change and the deoxidized hemoglobin concentration change are significant in the respective activity periods inputted from the setting-up section.

7. The living body light measuring device according to claim 1, wherein the calculator calculates a peak time of brain activity for each of oxidized hemoglobin and deoxidized hemoglobin,
the device further comprising a setting-up section for setting up a brain activity change period, the center of the change period being the peak time, and, on the basis of the brain activity change during the change period, the calculator deciding whether the oxidized hemoglobin concentration change and the deoxidized hemoglobin concentration change are each significant during the said change period.

8. The living body light measuring device according to claim 7, wherein the peak time is calculated from any one of an average waveform of brain activity waveforms at all of the measurement points, a brain activity waveform at the measurement point where the brain works most actively, a standard brain activity waveform, an average waveform of brain activity waveforms at sites to be measured, and a standard brain activity waveform prepared by past brain activity signals of the subject.

9. The living body light measuring device according to claim 1, wherein the display displays the decision at the measurement points stepwise based on the significances of oxidized hemoglobin and deoxidized hemoglobin.

10. The living body light measuring device according to claim 1, wherein the display displays a brain activity waveform at the measurement point where the oxidized hemoglobin concentration change or the deoxidized hemoglobin concentration change is most significant.

11. The living body light measuring device according to claim 1, wherein the calculator decides whether the oxidized hemoglobin concentration change, the deoxidized hemoglobin concentration change, and a change in the concentration of all hemoglobins are each significant at each statistically of the measurement points.

12. The living body light measuring device according to claim 1, wherein the measurement point is substantially at a middle point between the pair of the light-radiating means and the light-receiving means.

13. The living body light measuring device according to claim 1, wherein the plural light-radiating means and the plural light-receiving means are alternately arranged in a lattice form.

14. A living body light measuring device, comprising:
plural light-radiating means from which light is radiated to a head of a subject;
plural light-receiving means for detecting light which is transmitted through the head of the subject after radiation from the light-radiating means;
a calculator for calculating a change of concentration of oxidized hemoglobin and a change of concentration of deoxidized hemoglobin in the head of the subject at a measurement point comprising a pair of each of the plural light-radiating means and corresponding ones of the light-receiving means, wherein the measurement point includes a signal detected by the light-receiving means,
a display for displaying the calculations obtained from the calculator,
wherein the calculator decides whether the oxidized hemoglobin concentration change and the deoxidized hemoglobin concentration change are significant at each of the measurement points, and produces an activity index combined with the significance of the oxidized hemoglobin concentration change and the significance of the deoxidized hemoglobin concentration change, and
the display displays the activity index at each of the measurement points.

* * * * *

UNITED STATES PATENT AND TRADEMARK OFFICE
CERTIFICATE OF CORRECTION

PATENT NO. : 7,890,270 B2  Page 1 of 1
APPLICATION NO. : 12/392207
DATED : February 15, 2011
INVENTOR(S) : H. Sato et al.

It is certified that error appears in the above-identified patent and that said Letters Patent is hereby corrected as shown below:

ON THE TITLE PAGE

Please insert Item (30) Foreign Application Priority Data as follows:

--(30)  Foreign Application Priority Data

Jun. 14, 2004  (JP)  ........................................2004-174925--

Signed and Sealed this
Twenty-sixth Day of April, 2011

David J. Kappos
*Director of the United States Patent and Trademark Office*